United States Patent
Walsh et al.

(10) Patent No.: US 7,618,364 B2
(45) Date of Patent: Nov. 17, 2009

(54) CARDIAC WALL TENSION RELIEF DEVICE AND METHOD

(75) Inventors: Robert G. Walsh, Lakeville, MN (US); Paul Andrew Pignato, Stacy, MN (US); Ann Margaret Thomas, Plymouth, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 797 days.

(21) Appl. No.: 10/959,888

(22) Filed: Oct. 5, 2004

(65) Prior Publication Data

US 2006/0074373 A1 Apr. 6, 2006

Related U.S. Application Data

(63) Continuation-in-part of application No. 10/839,724, filed on May 4, 2004, now Pat. No. 7,326,174, which is a continuation of application No. 09/591,875, filed on Jun. 12, 2000, now Pat. No. 6,730,016, application No. 10/959,888, filed on Oct. 5, 2004, which is a continuation-in-part of application No. 09/591,754, filed on Jun. 12, 2000, now Pat. No. 6,902,522.

(51) Int. Cl.
*A61F 13/00* (2006.01)

(52) U.S. Cl. ........................................ 600/37

(58) Field of Classification Search ............ 600/16–18, 600/37; 128/897, 898
See application file for complete search history.

(56) References Cited

U.S. PATENT DOCUMENTS

| | | | |
|---|---|---|---|
| 5,702,343 A | 12/1997 | Alferness | |
| 6,059,715 A | 5/2000 | Schweich et al. | |
| 6,077,214 A * | 6/2000 | Mortier et al. | 600/16 |
| 6,123,662 A | 9/2000 | Alferness et al. | |
| 6,425,856 B1 | 7/2002 | Shapland et al. | |
| 6,463,332 B1 | 10/2002 | Aldrich | |
| 6,482,146 B1 | 11/2002 | Alferness et al. | |
| 6,508,756 B1 | 1/2003 | Kung et al. | |
| 6,572,533 B1 | 6/2003 | Shapland et al. | |
| 6,682,476 B2 | 1/2004 | Alferness et al. | |
| 6,692,458 B2 | 2/2004 | Forman et al. | |
| 6,730,016 B1 | 5/2004 | Cox et al. | |
| 7,174,896 B1 * | 2/2007 | Lau | 128/898 |
| 2002/0169360 A1 * | 11/2002 | Taylor et al. | 600/37 |
| 2003/0229265 A1 | 12/2003 | Girard et al. | |

(Continued)

FOREIGN PATENT DOCUMENTS

JP  2271829  11/1990

(Continued)

OTHER PUBLICATIONS

Ludwick, "Schlerosing Agents," Jul. 25, 2002, http://www.bcm.edu/oto/grand/07-25-02.htm, 11 pages, dated printed Oct. 27, 2004.

(Continued)

*Primary Examiner*—Samuel G Gilbert
(74) *Attorney, Agent, or Firm*—Faegre & Benson LLP

(57) ABSTRACT

Method and apparatus are disclosed for treating congestive heart failure by administering a fibrosis-inducing agent to an epicardial surface of the heart in an amount selected to induce the formation of fibrosis on the epicardial surface. The fibrosis-inducing agent may be a drug, metal, abrasive or an electrical stimulation on the epicardial surface.

18 Claims, 5 Drawing Sheets

U.S. PATENT DOCUMENTS

2004/0138521 A1     7/2004   Grabek et al.
2005/0165466 A1     7/2005   Morris et al.

OTHER PUBLICATIONS

Nishi, et al., "Hypoxia-Inducible Factor 1 Mediates Upregulation of Telomerase (hTERT)," *Molecular and Cellular Biology*, pp. 6076-6083 (Jul. 2004).

Minatoguchi, et al., "Acceleration of the Healing Process and Myocardial Regeneration May Be Important as a Mechanism of Improvement of Cardiac Function and Remodeling by Postinfarction Granulocyte Colony—Stimulating Factor Treatment," *Circulation*, pp. 2572-2580 (Jun. 2004).

Ohtsuka, et al., "Cytokine therapy prevents left ventricular remodeling and dysfunction after myocardial infarction through neovasculatrization," *FASEB*, vol. 18, pp. 851-853 (May 2004).

Zou, et al., "Leukemia Inhibitory Factor Enhances Survival of Cardiomyocytes and Induces Regeneration of Myocardium After Myocardial Infarction," *Circulation*, pp. 748-753 (Aug. 2003).

Nadal-Ginard, et al., "Myocyte Death, Growth, and Regeneration in Cardiac Hypertrophy and Failure," *Circulation*, pp. 139-150 (Feb. 2003).

Kajstura, et al., "Myocyte proliferation in end-stage cardiac failure in humans," *Proc. Natl. Acad. Sci. USA*, vol. 95, pp. 8801-8805 (Jul. 1998).

Liu, et al., "A possible role of initial cell death due to mechanical stretch in the regulation of subsequent cell proliferation in experimental vein grafts," *Biomechan. Model Mechanobiol.*, pp. 17-27 (2002).

Brietzke, S. et al., "Injection snoreplasty: How to treat snoring without all the pain and expense," *Otolaryngol Head Neck Surg.*, vol. 124, pp. 503-510 (May 2001).

\* cited by examiner

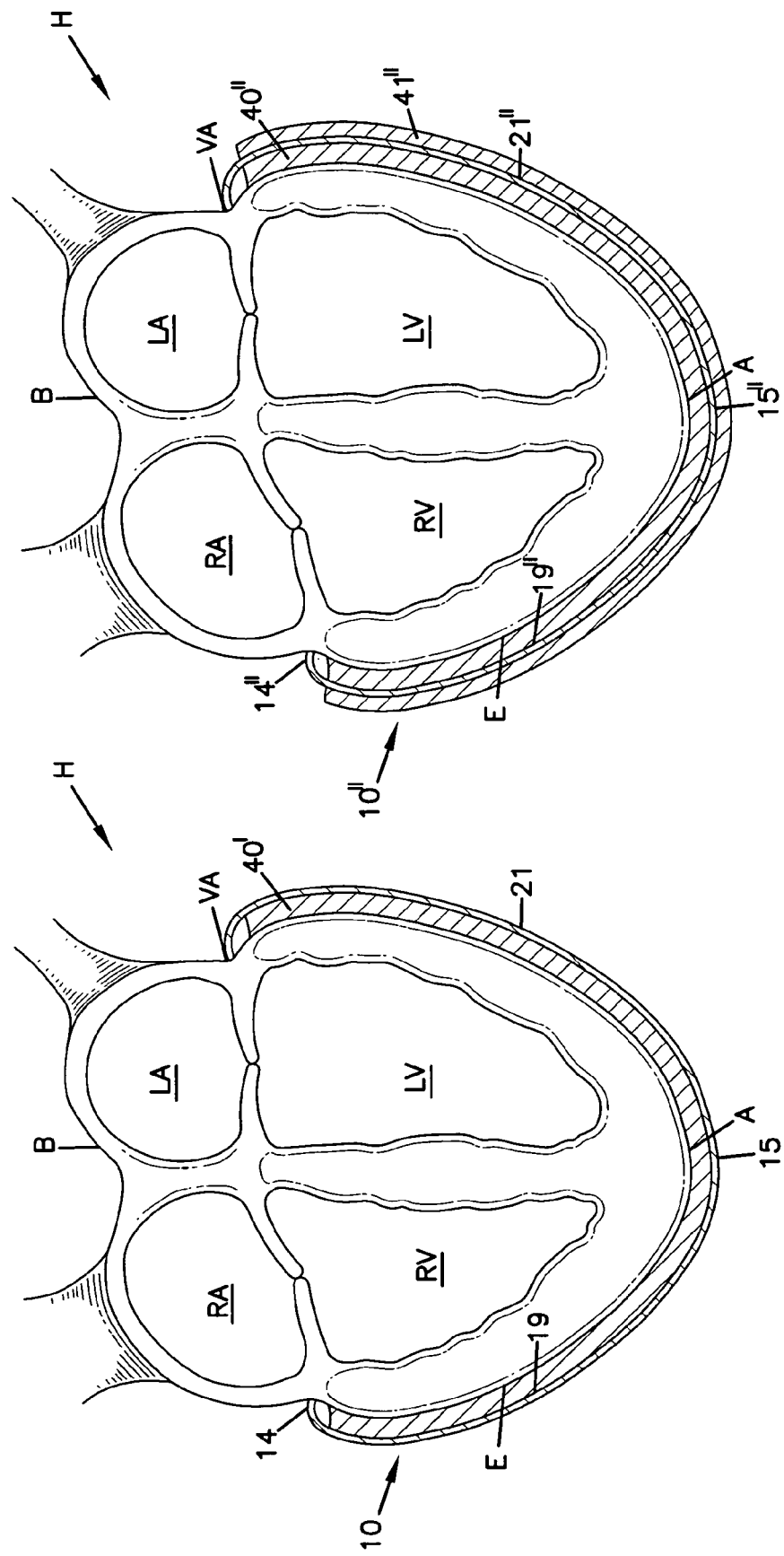

CARDIAC WALL TENSION RELIEF DEVICE AND METHOD

CROSS-REFERENCE TO RELATED APPLICATION

The present application is a continuation-in-part application of U.S. patent application Ser. No. 10/839,724, filed May 4, 2004, now U.S. Pat. No. 7,326,174 which is a continuation application of U.S. patent application Ser. No. 09/591,875, filed Jun. 12, 2000 (now U.S. Pat. No. 6,730,016 B1 issued May 4, 2004). The present application is also a continuation-in-part of U.S. patent application Ser. No. 09/591,754, filed Jun. 12, 2000, now U.S. Pat. No. 6,902,522 which applications are incorporated herein by reference.

I. BACKGROUND OF THE INVENTION

1. Field of the Invention

The present invention pertains to a method and apparatus for treating heart disease. More particularly, the present invention is directed to a method and apparatus for treating congestive heart disease and related valvular dysfunction and other complications associated with dilated cardiomyopathy. Further, the present invention is directed to treating heart disease with method and apparatus for relieving wall tension.

2. Description of the Prior Art

Congestive heart disease is a progressive and debilitating illness. The disease is characterized by a progressive enlargement of the heart. As the heart enlarges, the heart performs an increasing amount of work in order to pump blood with each heartbeat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood. Causes of congestive heart disease are not fully known. In certain instances, congestive heart disease may result from viral infections. In such cases the heart may enlarge to such an extent that the adverse consequences of heart enlargement continue after the viral infection has passed and the disease continues its progressively debilitating course.

Patients suffering from congestive heart disease are commonly grouped into four classes (i.e., New York Heart Association Classes I, II, III, and IV). In the early stages (for example, Classes I and II) drug therapy is the commonly prescribed treatment. Drug therapy treats the symptoms of the disease and may slow the progression of the disease. In later stages of heart failure progression, drug therapies may be without benefit. Importantly, there is no cure for congestive heart disease. Further, drugs may have adverse side effects.

Historically, the only permanent treatment for congestive heart disease has been heart transplant. Qualifying patients are in the later stages of congestive heart disease and are extremely sick individuals. Further, transplant patients must suffer through a risky transplant procedure which is extremely invasive and expensive and in many cases, only shortly extend the patient's lives. Also, and unfortunately, not enough hearts are available for transplant to meet the needs of congestive heart disease patients.

Many new techniques have been suggested for treating congestive heart failure and some of these techniques are in clinical study in advance of commercial availability of products and methods. An example of these are disclosed in Assignee's U.S. Pat. No. 5,702,343 issued Dec. 30, 1997; U.S. Pat. No. 6,123,662 issued Sep. 26, 2000; and U.S. Pat. No. 6,482,146 issued Nov. 19, 2002. These patents describe a technique for treating congestive heart failure by placing a cardiac support device in the form of a jacket around the heart. In certain of the specific embodiments disclosed, the jacket is a knit of polyester material which surrounds the heart and which provides resistance to progressive diastolic expansion. Other described materials include metal such as stainless steel. In certain aspects, the knit size and open cell size are selected to minimize or control fibrosis. It is believed that such resistance decreases wall tension on the heart and permits a diseased heart to beneficially remodel. Assignee's U.S. Pat. No. 6,730,016 issued May 4, 2004 describes a jacket with a non-adherent lining or coating. In certain embodiments, the coating is in specific locations (e.g., over surface-lying cardiac blood vessels). Assignee's U.S. Pat. No. 6,425,856 issued Jul. 30, 2002 describes a cardiac jacket with therapeutic agents incorporated on the jacket for providing additional therapy to the heart. The '856 patent also describes a jacket made of bio-resorbable material. Assignee's U.S. Pat. No. 6,572,533 issued Jun. 3, 2003 describes a treatment on the left ventricle side of the heart only. Assignee's U.S. patent application Ser. No. 10/165,504 filed Jun. 7, 2002 and published Dec. 12, 2003 and Publication No. 2003-0229265 A1 teaches a highly compliant cardiac jacket.

Other examples of wall tension relief are disclosed in U.S. Pat. No. 6,059,715 issued May 9, 2000 (assigned to Myocor Inc.) which describes various geometries for applying force to external surfaces of the heart to reduce wall tension on the heart. U.S. Pat. No. 6,508,756 issued Jan. 21, 2003 (assigned to Abiomed Inc.) describes a passive cardiac assistance device. U.S. Pat. No. 6,682,474 dated Jan. 27, 2004 also describes an expandable cardiac harness for treating congestive heart failure (assigned to Paracor Surgical Inc.). The '474 patent describes a harness made of nitinol.

In addition to mechanical devices for surrounding the heart, congestive heart failure is also being investigated for treatment through techniques for cardiac pacing of the heart (particularly so called by-ventricular pacing).

Notwithstanding the forgoing, treatments for congestive heart failure are under continuing investigation and consideration. It is an object of the present invention to provide improved methods and apparatus for treating congestive heart failure and complications related to dilated cardiomyopathy including valvular dysfunction.

II. SUMMARY OF THE INVENTION

According to the present invention, a method and apparatus are disclosed for treating congestive heart failure by administering a fibrosis-inducing agent to an epicardial surface of the heart in an amount selected to induce the formation of fibrosis on the epicardial surface. The fibrosis-inducing agent may be a drug, metal, abrasive or an electrical (or other physical) stimulation on the epicardial surface. In certain embodiments a protective layer prevents the agent from migrating to other organs in the thoracic cavity.

III. BRIEF DESCRIPTION OF THE DRAWINGS

FIG. 4 is the view of the heart of FIG. 1 treated with an alternative embodiment of the present invention;

FIG. 5 is the view of the heart of FIG. 1 treated with a still further alternative embodiment of the present invention;

IV. DETAILED DESCRIPTION OF THE PREFERRED EMBODIMENT

Figure 1:
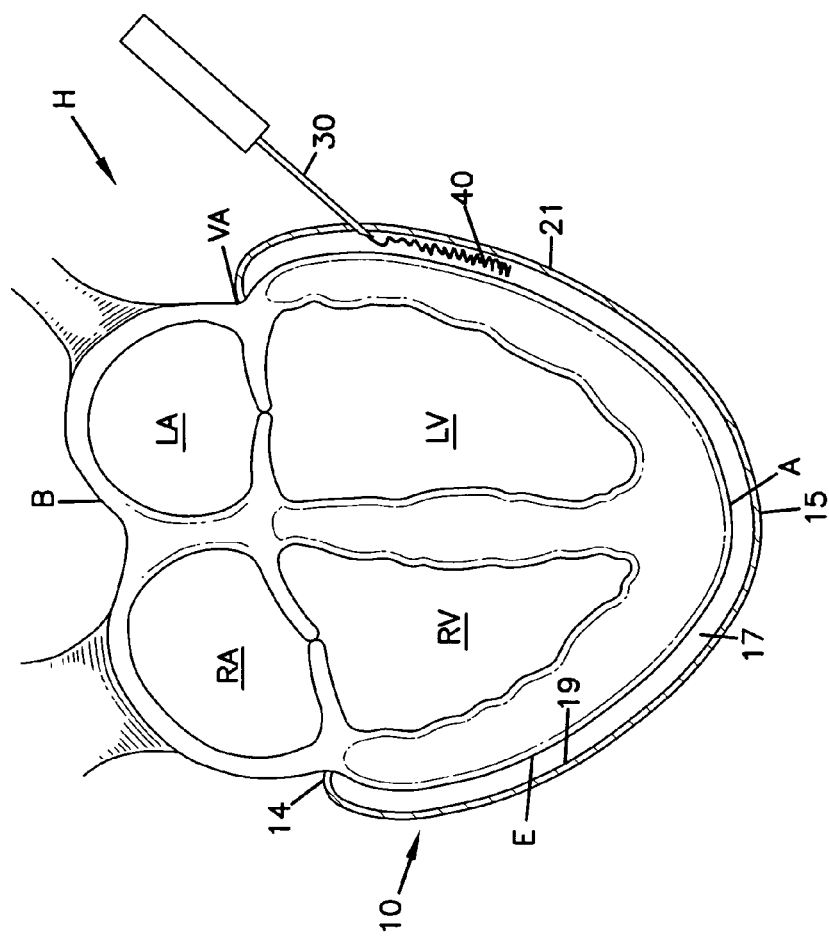
FIG. 1 is a sectional view of a human heart illustrating various anatomical features.

With reference to the various drawing figures in which identical elements are numbered identically throughout, a description of the preferred embodiment of the present invention will now be provided. Assignee's afore-mentioned U.S. Pat. Nos. 5,702,343; 6,123,662; 6,482,146; 6,730,016; 6,425,856 and 6,572,533 and U.S. patent application Publication No. 2003-0229265 A1 are incorporated herein by reference as though set forth in full. Further, The afore-mentioned U.S. Pat. Nos. 6,059,715; 6,508,756 and 6,682,474 are incorporated herein by reference as though set forth in full.

The present invention is directed toward treatment of congestive heart failure by promoting the formation of a controlled amount of epicardial fibrosis to inhibit cardiac dilatation. The promotion of fibrosis can promote a process of fibrous contracture in which specialized cells identified as myofibroblasts participate in the biological process by which the surface area of the fibrous layer is reduced. Such cells have a characteristic phenotype, which can be demonstrated, for instance, by an appropriate stain to identify alpha-smooth muscle actin, which serves a contractile function.

Cardiomyocyte replication is of potential importance toward the inducement or inhibition of heart failure progression. This is especially the case with respect to the impact of cardiac constraint therapy on cell replication. It is contended that cell content in the heart is influenced by two primary processes, namely, cell loss and cell replication and recruitment. Cell loss can result from injury (such as promoted by acute or chronic ischemia, viral infection, genetic predisposition, etc.). Likewise increase in cell content can result from replication of cells in situ, or recruitment of cells from other parts of the body.

Scientific and clinical literature suggests that a small portion of native cardiomyocytes are signaled to replicate when the heart is under stress as occurs during heart failure progression, and that cell proliferation may be a determinant of deleterious ventricular remodeling. Accordingly, the rates of cell replication would decrease, in response to successful therapy (such as with a cardiac constraining device) following implant of a cardiac constraining device, which is intended to reduce ventricular wall stress, thus decreasing the potential for ventricular remodeling. It is contended that an elevated rate of cell replication within a heart could serve a beneficial purpose for a heart upon which a cardiac constraining device is implanted. In this case, instead of cell replication promoting deleterious ventricular remodeling, it is contended that cell replication could serve to beneficially replace myocardial cellular mass lost during disease progression. Therefore, if it is desired to retain an elevated rate of cell replication (and the potential for myocardial repair afforded by cell replication), then an understanding of the signaling processes involved in up- and down-regulation of cell replication needs to be revealed. The signaling mechanisms for such processes do not appear to be known at the present time, but are likely to be multi-factorial. Integrin signaling may be involved, as well as pathways involving hypoxia signaling. Ventricular wall stress, resulting from cardiac dilation, results in an increase in tissue oxygen stress. Therefore, signals operating in hypoxia might serve to retain elevated rates of cell replication and stressed myocardium.

Referring now to FIG. 1, a human heart H is schematically shown in cross-section and illustrating a left ventricle LV, a right ventricle RV, a left atria LA and a right atria RA. The atria LA, RA are separated from the ventricles LV, RV by a valvular annulus VA region in the region of heart valves. The heart extends from a lower apex A to an upper base B. The exterior surface of the heart H is the epicardium or epicardial surface E.

In the following discussion of a preferred embodiment, the treatment of the present invention is being described as treating the heart H in the region of the ventricles LV, RV (i.e., between the valvular annulus VA and the apex A). However, it will be appreciated the treatment and described apparatus can be applied to the atria LA, RA between the annulus VA and the base B either alone or in combination with a ventricular region treatment. Further, while in a preferred embodiment the treatment of the present invention and associated apparatus are shown surrounding the heart and covering both the left and right ventricles LV, RV, only one or other of the left ventricle LV and right ventricle RV could be so treated and covered.

As will be described, the present invention is directed to various apparatus and methods to treat congestive heart failure and related diseases by encouraging fibrosis on the epicardial surface of the heart. In several embodiments, this is described in combination with a jacket surrounding the heart. In a preferred embodiment, and unlike the teachings of the afore-mentioned patents, the jacket (or other wrap) is non-constraining in that it selected to be so loosely fitting or have such a high degree compliance that the jacket or wrap would not present resistance to heart expansion during diastole or assist to contraction during systole. However, and as described, the teachings of the present invention could be applied to the afore-mentioned cardiac support devices or harnesses and provide a force either resisting in limited manner diastolic expansion or assisting systolic contraction.

Figure 2:
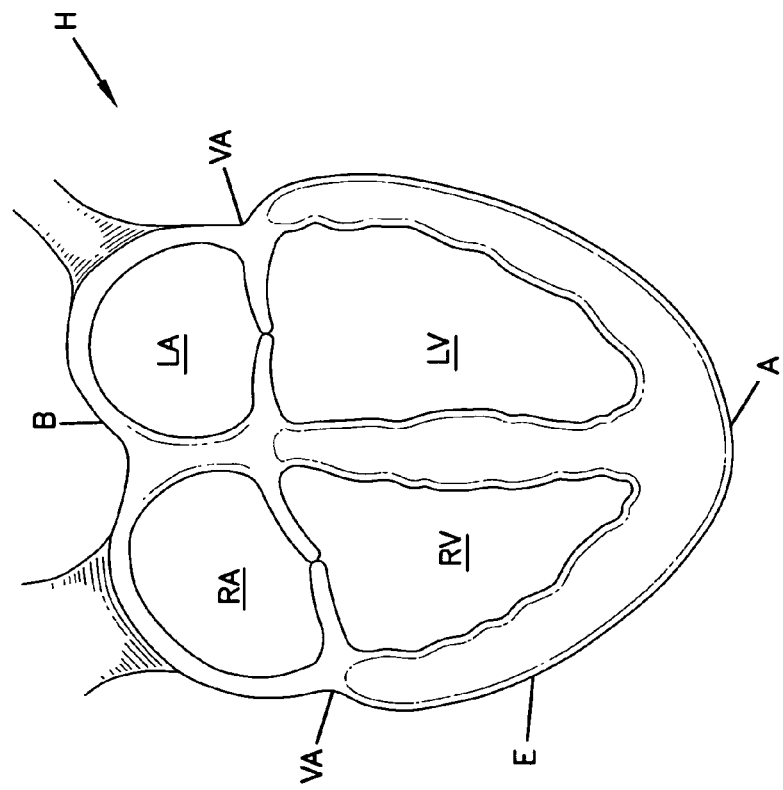
FIG. 2 is the view of the heart of FIG. 1 treated with a jacket according to the present invention.
Figure 3A:
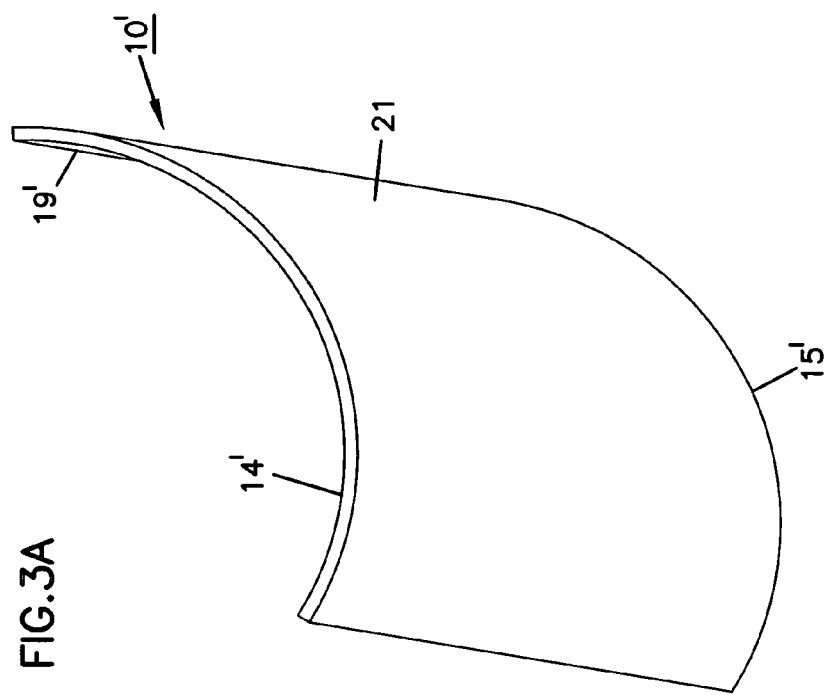
FIG. 3A is a perspective view of an alternative construction of a jacket.
Figure 3:
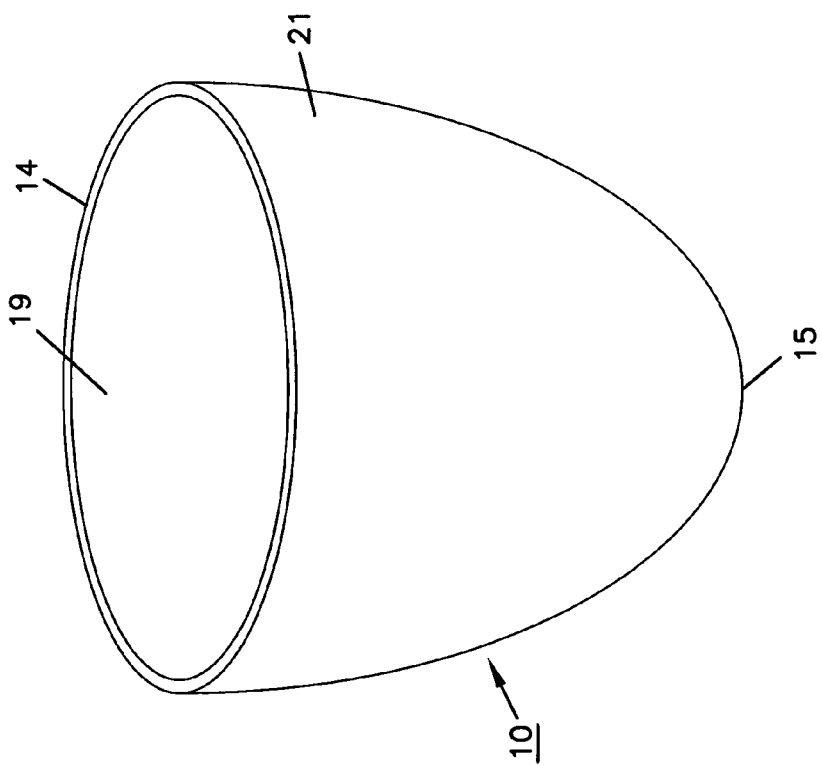
FIG. 3 is a perspective view of the jacket of FIG. 2.

In a first embodiment, a jacket 10 is provided having a thin membrane 12 sized to be placed around the heart covering the epicardial surface of the heart and opposing the epicardial surface around both the left and right ventricle. In FIG. 2, the jacket is shown in place on the heart H. In FIG. 3, the jacket 10 is shown alone.

Preferably, the jacket 11 has a generally hollow, conical shape with an open base end 14 such that the jacket 10 can be slipped over the apex A of the heart H. The length of the jacket (distance from its apex 15 to its base 14) is selected for the jacket 10 to extend from the heart apex A to the valvular annulus VA to surround the ventricles LV, RV.

The jacket 10 may be a bio-compatible flexible material with is highly compliant or may be a more rigid material sized greater than the heart H to permit non-constricting enlargement of the heart H throughout the cardiac cycle. Opposing surfaces of the interior surface 19 of the jacket 10 and the epicardial surface E define an open space 17. In the embodiment shown, the jacket 10 has a closed apex 15. However, the apex 15 could be open to expose the apex A of the heart H when the jacket 10 is in place.

In a preferred embodiment, the present invention is described in the form of a preformed jacket 10 sized and shaped to surround the heart H for ease of placement. However, the present invention could be formed in a sheet material 10' (FIG. 3A) having an upper end 14', lower end 15' and interior surface 19'. The sheet 10' is wrapped around the heart (or diseased area of the heart) by a physician and kept in place through any suitable means such as sutures or the like. The wrap 10' is placed loosely with the upper edge 14' at the valvular annulus VA and with the lower edge 15' covering or near the apex A. Alternate method of device attachment include bio-adhesives. Such adhesives would serve either as fibrosis promoting (or preventing depending upon the selected adhesive) resulting in a mask/pattern of fibrotic promotion.

Preferably, the jacket membrane 10, 10' is non-porous. By non-porous it is meant that the jacket 10, 10' will not pass agents as will be described from the interior side 19, 19' of the jacket facing the epicardial to the outer or exterior side 21, 21' of the jacket facing away from the epicardial surface E of the heart H. Therefore, in this context, "non-porous" means a sufficiently low porosity to resists passage of such agents through the wall of the jacket 10, 10'.

The jacket 10, 10' creates the space 17 between the interior surface 19, 19' and the epicardium E. Into this space 17, fibrosis-inducing therapeutic agents can be placed to promote epicardial fibrosis. A representative examples of such a fibrosis-inducing agents can be a sclerosing agent (such as those described in Brietzke et al., Injection Snoreplasty: How to Treat Snoring Without All The Pain and Expense", *Otolaryngology*, pp. 503-510. Also, such agents can be any substance such as a polymer, metal, abrasive or the like which is selected to promote epicardial fibrosis. Representative sclerosing/fibrosing agents could include sodium tetradecyl sulfate (Sotradecol, Thromboject), bleomycin, polyoxy-ethyl 9 lauryl ether (polidocanol), ethanol, or talc (magnesium silicate hydroxide. Agents could also include polymer sheets, films, scaffolds, matrixes, etc, fabricated from polyester, PTFE, polyethylene, polypropylene, piezoelectric metals or polymers, other metals, or various other structural materials having history as implant materials. Another such agent is erythromycin. A discussion of sclerosing agents is set forth in Ludwick, "Sclerosing Agents", Jul. 25, 2002, at Baylor College of Medicine (Houston, Tex.) website: http://www.bcm.edu/oto/grand/07-25-02.htm.

In the embodiment of FIG. 2, the therapeutic agents 40 are provided in a liquid or injectable form. The agents 40 are admitted to the space 17 by injection from a needle 30 passed into the space 17 through the jacket 10. The needle 30 is preferably a non-coring needle and the material of the jacket is self-sealing (as is well known in the art) to seal and prevent leakage after removal of the needle 30. Within the space 17, the agents 40 are free to contact and react with the epicardial surface E. The agents 40 interact with the surface E to promote growth of fibrosis. Such fibrosis is natural to the body and is believed by applicant to provide wall tension relief as well as promote myocyte production or migration.

Agents might be delivered by various different means, including percutaneous via catheter, or by intraveneous injection, subcutaneous injection, or oral administration. The object is to define a specific agent intended to promote or inhibit fibrosis in the area surrounding the heart, where a fibrotic process would normally be promoted by contact of tissue with the implanted device.

It can be stated that fibrosis is associated with cell proliferation—principally fibroblasts. Cell proliferation requires establishment/enhancement of the local circulatory system to supply oxygen and nutrients. New blood supply is stimulated by signaling molecules such as cytokines released by proliferating cells. A contention, but not proven is that these signal molecules could also influence development of new blood vessels in ischemic or infarcted myocardium physically removed from the epicardial surface as well.

As an alternative to needle injection (and as illustrated in FIG. 4), the fibrosis-inducing therapeutic agents 40' can be applied to the interior surface 19 of the membrane 10, 10' before placement over the heart H. The fibrosis-inducing agent can be delivered via a controlled-release mechanism utilizing a matrix or scaffold attached to the interior side 19 of the membrane 10 which would release the agent in much the same way as a drug-eluding stent.

The relatively non-porous nature of the membrane 10 material means that the membrane 10 contains the agent 40, 40' between the epicardial surface E and the membrane interior surface 19. This resists excessive leakage of the agent 40, 40' to the outside of the membrane 10, 10. Such leakage could result in the agent 40, 40' coming in contact with other organs (e.g., lungs) within the thoracic cavity of the patient. This contact could result in undesirable adhesion formation between organs of the thoracic cavity.

A still further alternative embodiment of the present invention is illustrated in FIG. 5. FIG. 5 shows a thin membrane material jacket 10". On the interior surface 19", a fibrosis-promoting agent 40" as previously described is provided for promoting fibrosis on the epicardial surface E. An exterior surface 21" of the membrane 10" is provided with a second agent 41" maintained in a scaffolding or matrix on the exterior surface 21" of the membrane 10". The second agent 41" is released away from the jacket 10" toward the thoracic space. The second agent is selected to inhibit fibrosis formation and inhibit adhesion formation. Representative examples of such fibrosis-inhibiting agents may include those recited in U.S. Pat. No. 6,425,856 issued Jul. 30, 2002 (e.g., those listed in col. 17, lines 34-42).

Agents 40, 40', 40" which can be placed within the space between the membrane 10, 10', 10" and the epicardial surface E or mounted on the interior surface of the membrane 10, 10', 10" include metallic objects (such as fabricated from stainless steel, titanium or nitinol or other metals in various shapes) which can be placed in direct contact with epicardium in order to stimulate epicardial surface fibrosis. The use of metals permits controlling the amount of metallic surface engaged in the epicardial surface and the geometry to control both the amount of fibrosis and the location of fibrosis. For example, it would be desirable if possible to avoid fibrosis directly over major cardiac arteries such that a surgeon may have access to such arteries for any future bypass or other vascular procedure.

Additionally and as an alternative embodiment, the membrane 10 can also be formed of a resorbable or bioresorbable material, which can release a fibrosis-inducing agent over time. In this embodiment, the fibrosis-inducing agent is not a separate layer but is incorporated into the material of the jacket. Biodegration of a resorbable polymer would promote surface fibrosis on the epicardium E which would in turn inhibit dilation associated with cardiomyopathy.

Figure 6:
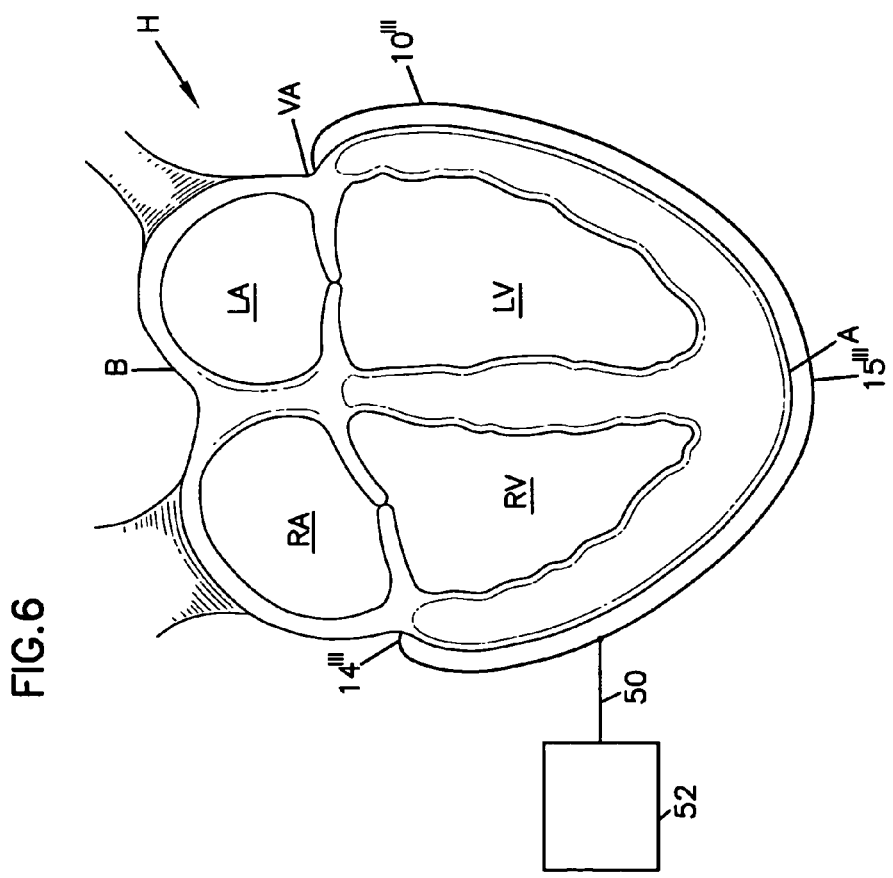
FIG. 6 is the view of the heart of FIG. 1 treated with a yet further alternative embodiment of the present invention.

A still further embodiment (FIG. 6) of the present invention is to form the jacket 10''' (which may be constricting or non-constricting) from an electrically conductive polymer, polymer/metal composite or from metal. The jacket 10''' is connected by leads 50 to a source 52 of an electrical signal.

The source 52 may be an implantable battery operated signal generator. The electrical signal is selected to promote growth of fibrosis. It will be understood that stimulation in this sense is not timed with any contractility of the heart and is not a pacing stimulation but a stimulation to promote fibrosis at the epicardial surface E. The stimulation agent can be any approach that uses a physical stimulus to promote fibrosis (such as ultrasonic energy, light/laser, IR, UV, cryogenics, radiofrequency, high-intensity microwave or heat.

In addition to the forgoing, the jacket 10 can be made abrasive by incorporating calcium carbonate or abrasive material onto the interior surface 19 of the device 10. The abrasive is the agent and eliminates the need for injection of a separate agent. The natural cardiac motion against the abrasive material provides a mechanical surface irritant to the epicardium which promotes surface fibrosis. An example of an abrasive material for such use is hydroxyapatite One undesirable effect of promoting epicardial surface fibrosis is that such fibrosis would interfere with the ease of identifying the location of superficial coronary arteries. Such visualization normally aids in efforts to perform anastomoses as part of coronary artery bypass surgery.

Figure 7:
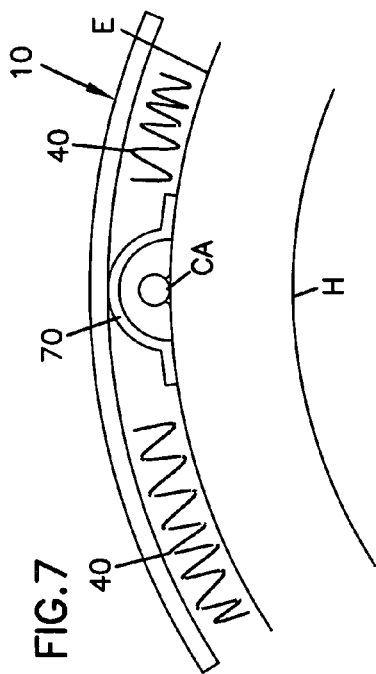
FIG. 7 is a side sectional view of a heart wall with a protective bridge according to the present invention.

According to the present invention, this may be avoided by use of coronary bridge devices 70 in FIG. 7. Such coronary bridge devices 70 may be fibrosis inhibiting materials or layers which can be placed over the coronary arteries or veins (e.g., coronary artery CA in FIG. 7) at the time of placing the jacket 10 or can be a physical bridge 70 as shown placed over the arteries CA to avoid any surface contact between the jacket 10 or any fibrosis-inducing agents 40 with the coronary arteries CA.

Figure 8:
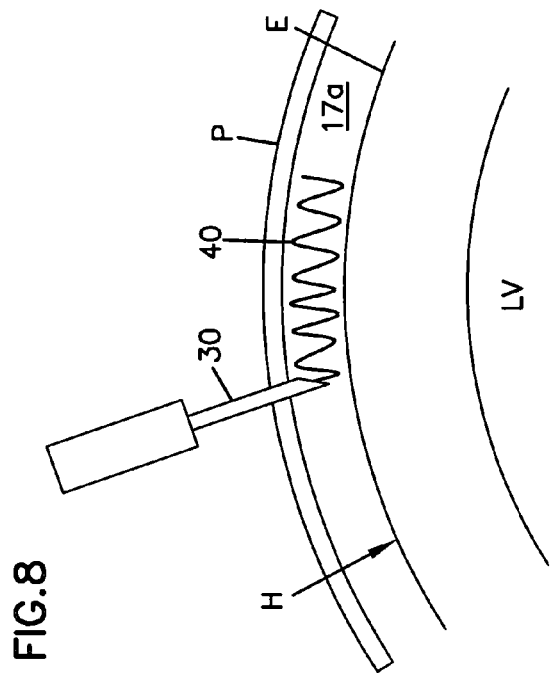
FIG. 8 is a side sectional view of a heart wall with a natural pericardium and a further embodiment of the present invention.

FIG. 8 shows a still further embodiment of the present invention where the patient's natural pericardium P is shown in relation to the heart H and defining a space 17a between the epicardial surface E and the pericardium P. The fibrosis inducing agents 40 are injected into the space 17a through injection needle 30 or the like to promote fibrosis on the epicardial surface.

Figure 9:
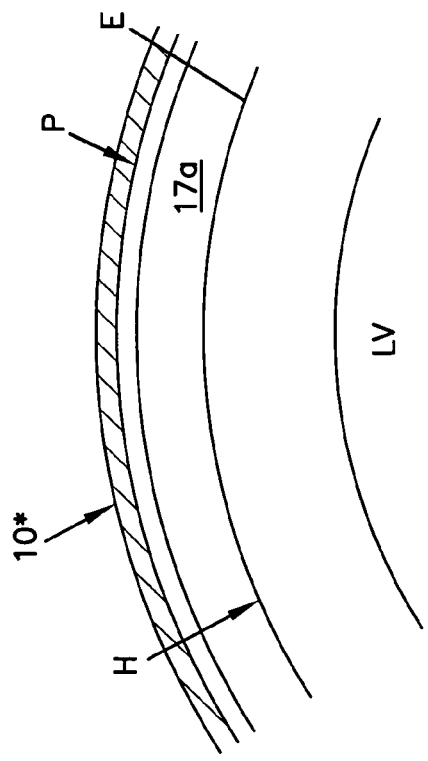
FIG. 9 is the view of FIG. 8 showing treating a pericardium with any of the embodiments of FIGS. 2-6.
Figure 10:
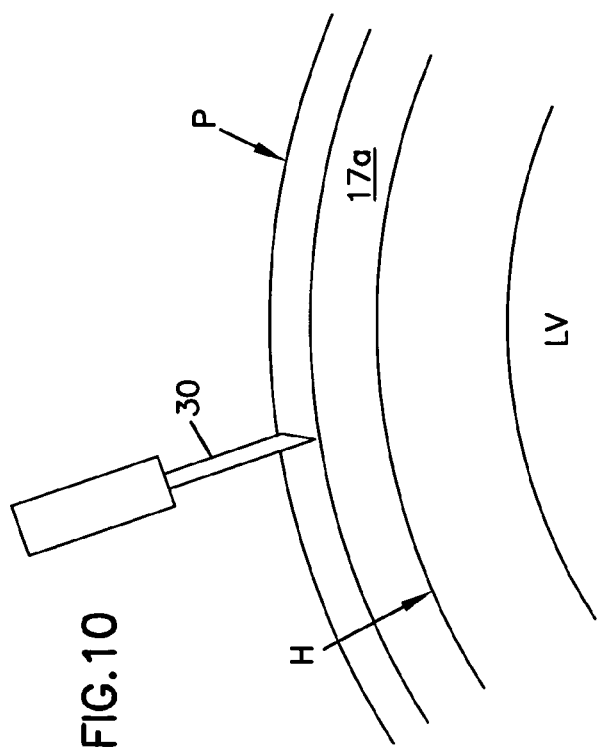
FIG. 10 is the view of FIG. 8 showing treating a pericardium with an injection of a fibrosis-inducing agent.

FIG. 9 shows an embodiment where an apparatus 10* according to any of the preceding embodiments of apparatus 10, 10', 10" or 10'" is applied to an outer surface of the pericardium P. In this embodiment, the pericardium P is stiffened and relieves wall tension on the heart H. FIG. 10 illustrates stiffening the pericardium P with direct injection from a needle 30 of a fibrosis-inducing agent as previously described. In treating the pericardium, an option is to treat only the thoracic side. This avoids creating adhesions between the inner surface of the pericardium and the heart or major vessels).

A modified version of a jacket could be provided for placement around the outside of an intact pericardium. Such a device could be in the form of a band or multiple bands running in a circumferential direction. The bands would be wide enough to afford broad support to the underlying heart, but thin enough to enable easy implant without interference with ligament or nerve attachments to the pericardium. Such devices could also be applicable for patients following cardiac surgery, if the native pericardium is partially or fully reapproximated following surgery. Reapproximation of the pericardium may be facilitatde by one of various methods known in the art.

An additional fibrosis-inducing agent and process are glutaraldehyde fixation (the same tanning process used for tissue heart valves).

Having disclosed the invention of preferred embodiment, it will be appreciated that modifications and equivalents of the disclosed concepts may occur to one of ordinary skill in the art having the benefit of the teachings of the present invention.

For example, a jacket as described is believed to alter the rates of cell loss (apoptosis, necrosis) and cell gain (through replication of cells in situ, or recruitment of cells from outside myocardium). The basic premise is to use the jacket as a passive constraint to reduce ventricular wall stress. A reduction in ventricular wall stress would translate to a decrease in oxygen stress within the tissue, and an improvement in mitochondrial integrity and cellular metabolic energetics. Such changes would serve to decrease the rate of cell loss through stress mechanisms. However, stress is thought to be a stimulant for cell replication under some circumstances, as well. Therefore, the signaling molecules that respond to hypoxia/oxidative stress may be up-regulated in myocardial cells during periods of stress. These signals would in tern tend to up-regulate cell division. Therefore, the elevated rates of cell replication thought to be present during heart failure progression would be down-regulated, perhaps towards normal, once stress had been reduced or removed. As a result, one possible way of promoting myocardial cell replication, following reduction in ventricular wall stress by passive containment, would be to adapt a jacket as described to serve as a platform for delivery of one or more agents that would tend to continue to promote cell replication, after the stress trigger has been removed. Such agents might include hypoxia-inducible factor 1 (HIF-1), which has been linked to promotion of cell replication under hypoxic conditions (Nishi H, Nakada T, Kyo S, Inoue M, Shay J W, Isaka K. "Hypoxia-inducible factor 1 mediates upregulation of telomerase (hTERT)", *Mol Cell Biol.* 2004 July; 24(13):6076-83).

Use of a jacket 10 as a scaffold for therapies permits additional alternative embodiments to promote beneficial reverse remodeling of the heart. These include implanting a scaffold around the heart containing cardiomyocytes grown in culture. Also, addition of a 3-dimensional scaffold across the heart surface would add bulk and thickness to the heart wall, tending to reduce wall stress (according to the LaPlace formula). In addition, long-term response might involve cells from the scaffold replicating in situ adding bulk, or migrating of cells from the implant to the heart, where these cells could also undergo integration/replication within the myocardium. Further, cells within the scaffold may be stimulated (via implanted pacemaker) to aid contraction of the heart. The cell/matrix implant would serve in much the same way that skeletal muscle would serve in dynamic cardiomyoplasty.

A further improvement would be to combine surgical methods intended to reshape the ventricle (such as represented by surgical anterior ventricular restoration (SAVR)) with implantation of the jacket. This would be similar in concept to implanting the jacket following removal of LVAD (left ventricular assist device), after successful bridge-to-recovery therapy. The intent is to keep the heart from undergoing chronic redilation after surgery.

Several ideas may be particularly attractive for acute myocardial infarction. In this case, the jacket's 10 function would be directed towards preventing cardiac remodeling prompted by acute myocardial infarction (heart attack). It is envisioned that such a device may not need to be a permanent device. In such case, the jacket 10 would resorb over several months, during which time, drug could be released. Such drugs could include of cytokines, growth factors, or transcription factors—either as proteins or genes. One attractive drug would be granulocyte colony-stimulating factor (G-CSF), (Minatoguchi S, Takemura G, Chen X H, Wang N, Uno Y, Koda M, Arai M, Misao Y, Lu C, Suzuki K, Goto K, Komada A, Takahashi T, Kosai K, Fujiwara T, Fujiwara H. Acceleration of the healing process and myocardial regeneration may be important as a mechanism of improvement of cardiac function and remodeling by postinfarction granulocyte colony-stimulating factor treatment. Circulation. 2004 Jun. 1; 109 (21):2572-80, Ohtsuka M, Takano H, Zou Y, Toko H, Akazawa H, Qin Y, Suzuki M, Hasegawa H, Nakaya H, Komuro I. Cytokine therapy prevents left ventricular remodeling and dysfunction after myocardial infarction through neovascularization. FASEB J. 2004 May; 18(7):851-3. Epub 2004 Mar. 4) Another possible agent for delivery would be leukemia inhibitory factor (LIF), (Zou Y, Takano H, Mizukami M, Akazawa H, Qin Y, Toko H, Sakamoto M, Minamino T, Nagai T, Komuro I. Leukemia inhibitory factor enhances survival of cardiomyocytes and induces regeneration of myocardium after myocardial infarction. Circulation. 2003 Aug. 12; 108(6):748-53. Epub 2003 Jul. 14.) Also, see review article (Nadal-Ginard B, Kajstura J, Leri A, Anversa P. Myocyte death, growth, and regeneration in cardiac hypertrophy and failure. Circ Res. 2003 Feb. 7; 92(2):139-50). A quote from p. 142 states: "Interestingly, the renewal rate (for cells) increases significantly under a variety of pathological conditions characterized mainly by an increase in cardiac wall stress".

Other drugs to deliver would fall under the general category of anti-fibrotics. Their use would be to inhibit surface formation of fibrosis—an unneeded and unwanted side effect of implanting biodegradable polymers. In the case of acute myocardial infarction, surface fibrosis would not be needed since fibrotic contracture to reduce heart size would not be necessary. Examples of anti-fibrotics could include rapamycin (sirolimus) and paclitaxel.

Angiogenic agents such as VEGF, FGF, or transcription factors which could up-regulate expression of these growth factors, would have particular value in the setting of acute myocardial infarction in order to aid healing and reestablishment of normal myocardial physiology.

Several additional references lend support to the concept that stress/heart failure progression would tend to increase the rate of myocyte replication, and that removal of stress (by putting a passive restraint around the heart) would tend to down-regulate the rate of cell replication. For example, Kajstura J, Leri A, Finato N, Di Loreto C, Beltrami C A, Anversa P. Myocyte proliferation in end-stage cardiac failure in humans. Proc Natl Acad Sci USA. 1998 Jul. 21; 95(15):8801-5. Also, Liu S Q, Ruan Y Y, Tang D, Li Y C, Goldman J, Zhong L. A possible role of initial cell death due to mechanical stretch in the regulation of subsequent cell proliferation in experimental vein grafts is detailed in the literature. Biomech Model Mechanobiol. 2002 June; 1(1):17-27.

The fibrosis location and orientation can be controlled. The agents can be deposited in a pattern to promote fibrosis on the CSD in such a way that the agents promote a non-uniform distribution of fibrotic response. It may be advantageous to promote fibrosis over certain areas of the epicardium, but not others—for instance the right ventricle vs. the left ventricle, over the top of an infarct scar vs. viable myocardium adjacent to an infarct scar. Specific areas might be preferably avoided for fibrotic tissue formation on the epicardial surface, such as along septal borders or overlying coronary arteries. Use of agents and locations of agents on the jacket can be selected to direct the type of fibrotic response (thickness, maturity, orientation, location) on the epicardial surface.

The structure of jacket (e.g., a mesh size of the jacket in the afore-mentioned patents of the assignee of the present invention could be enlarged or made smaller) to direct fibrotic response in such a way that the fibrosis has a specific orientation—that is, the cells, and extracellular matrix have directionality. Such directionality would be preferred in the circumferential direction, so that fibrotic contracture would be directed primarily in the circumferential direction, as opposed to the longitudinal direction.

In addition to promoting fibrotic response to enable fibrotic contracture for cardiac applications, the present invention can be applied to other applications such as ascending/descending aortic aneurysms, stomach, lung, or other indications which can be treated by fibrotic growth.

While a jacket, membrane or needle have been specifically described for delivery of agents other techniques of agent delivery could be employed (such as catheter, transcutaneous (subcostal, thoracic, sternal, catheter)).

It is intended that such modifications and equivalents shall be included within the scope of the appended claims.

We claim:

1. An apparatus for treating a condition of a heart comprising:

a carrier of bio-compatible and bio-resorbable material sized and shaped to be placed over at least a portion of an epicardial surface of said heart and to surround and cover at least a substantial portion of a left and right ventricle of the heart, with a first surface of said carrier opposing said epicardial surface and a second surface opposite the first surface;

a fibrosis-inducing agent disposed on said first surface of the carrier with said fibrosis-inducing agent selected to induce the formation of fibrosis on said epicardial surface; and wherein the apparatus prevents the fibrosis-inducing agent from inducing the formation of fibrosis on tissue in contact with the second surface of the carrier.

2. An apparatus according to claim 1 wherein said material is impermeable to said agent.

3. An apparatus according to claim 1 further comprising a fibrosis-inhibiting agent on the second surface of said carrier.

4. An apparatus according to claim 1 wherein said agent is an abrasive.

5. An apparatus according to claim 1 wherein said agent is a sclerosing agent.

6. An apparatus according to claim 1 wherein said agent is a metal.

7. An apparatus according to claim 1 wherein the carrier includes elastic and compliant material.

8. An apparatus according to claim 7 wherein the elastic and complaint material comprises an open cell material.

9. An apparatus according to claim 8 wherein the material further includes material impermeable to the fibrosis-inducing agent.

10. An apparatus according to claim 9 further comprising a fibrosis-inhibiting agent on the second surface of the carrier.

11. An apparatus according to claim 1 wherein:

the carrier material is impermeable to the fibrosis-inducing agent; and the apparatus further includes a fibrosis-inhibiting agent on the second surface of the carrier.

12. An apparatus according to claim 11 wherein the carrier includes elastic and complaint material.

13. An apparatus according to claim 12 wherein the apparatus is configured to avoid contact between the fibrosis-inducing agent and coronary arteries or veins.

14. An apparatus according to claim 12 and including bridge structures on the carrier to avoid contact between the fibrosis-inducing agent and coronary arteries or veins.

15. An apparatus according to claim 11 wherein the apparatus is configured to avoid contact between the fibrosis-inducing agent and coronary arteries or veins.

16. An apparatus according to claim 11 and including bridge structures on the carrier to avoid contact between the fibrosis-inducing agent and coronary arteries or veins.

17. An apparatus for treating a condition of a heart comprising:
- a carrier of bio-compatible material sized and shaped to be placed over at least a portion of an epicardial surface of said heart and to surround and cover at least a substantial portion of a left and right ventricle of the heart, with a first surface of said carrier opposing said epicardial surface and a second surface opposite the first surface;
- a fibrosis-inducing agent disposed on said first surface of the carrier with said fibrosis-inducing agent selected to induce the formation of fibrosis on said epicardial surface; and wherein the apparatus prevents the fibrosis-inducing agent from inducing the formation of fibrosis on tissue in contact with the second surface of the carrier, and wherein the apparatus is configured to avoid contact between the fibrosis-inducing agent and coronary arteries or veins.

18. An apparatus for treating a condition of a heart comprising:
- a carrier of bio-compatible material sized and shaped to be placed over at least a portion of an epicardial surface of said heart and to surround and cover at least a substantial portion of a left and right ventricle of the heart, with a first surface of said carrier opposing said epicardial surface and a second surface opposite the first surface;
- a fibrosis-inducing agent disposed on said first surface of the carrier with said fibrosis-inducing agent selected to induce the formation of fibrosis on said epicardial surface; and wherein the apparatus prevents the fibrosis-inducing agent from inducing the formation of fibrosis on tissue in contact with the second surface of the carrier; and
- bridge structures on the carrier to avoid contact between the fibrosis-inducing agent and coronary arteries or veins.

* * * * *

UNITED STATES PATENT AND TRADEMARK OFFICE
CERTIFICATE OF CORRECTION

PATENT NO. : 7,618,364 B2 Page 1 of 1
APPLICATION NO. : 10/959888
DATED : November 17, 2009
INVENTOR(S) : Walsh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1349 days.

Signed and Sealed this

Nineteenth Day of October, 2010

David J. Kappos
*Director of the United States Patent and Trademark Office*